(12) United States Patent
Xu et al.

(10) Patent No.: US 11,213,213 B2
(45) Date of Patent: Jan. 4, 2022

(54) SYSTEMS AND METHODS OF COMBINED OPTICAL COHERENCE TOMOGRAPHY AND PRESSURE MEASUREMENT

(71) Applicant: KOTL, LLC, Acton, MA (US)

(72) Inventors: Chenyang Xu, Devens, MA (US); Wei Kang, Somerville, MA (US)

(73) Assignee: KOTL, LLC, Devens, MA (US)

( * ) Notice: Subject to any disclaimer, the term of this patent is extended or adjusted under 35 U.S.C. 154(b) by 506 days.

(21) Appl. No.: 16/364,597

(22) Filed: Mar. 26, 2019

(65) Prior Publication Data

US 2020/0305732 A1 Oct. 1, 2020

(51) Int. Cl.
*A61B 5/0215* (2006.01)
*A61B 5/00* (2006.01)
*G02B 6/02* (2006.01)
*G02B 6/036* (2006.01)

(52) U.S. Cl.
CPC ........ *A61B 5/02154* (2013.01); *A61B 5/0066* (2013.01); *A61B 5/0084* (2013.01); *G02B 6/02042* (2013.01); *G02B 6/03633* (2013.01); *G02B 6/03644* (2013.01); *A61B 2562/0238* (2013.01); *A61B 2562/0242* (2013.01)

(58) Field of Classification Search
CPC .......... A61B 5/0066; A61B 2562/0247; G02B 6/02042
See application file for complete search history.

(56) References Cited

U.S. PATENT DOCUMENTS

| 5,077,815 A | 12/1991 | Yoshizawa et al. |
| 8,478,384 B2 | 7/2013 | Schmitt et al. |
| 2010/0021114 A1 | 1/2010 | Chen et al. |
| 2011/0205349 A1 | 8/2011 | Li |
| 2014/0094697 A1* | 4/2014 | Petroff ................. A61B 5/0066 600/427 |
| 2016/0220131 A1* | 8/2016 | Kishida .............. G01D 5/35364 |
| 2017/0112384 A1* | 4/2017 | Maswadi .................. A61B 8/12 |

OTHER PUBLICATIONS

David A. B. Miller, "All linear optical devices are mode converters", Opt. Express 20, 23985-2399., 6 pages, 2012.

(Continued)

*Primary Examiner* — Yi-Shan Yang
(74) *Attorney, Agent, or Firm* — Sunstein LLP

(57) ABSTRACT

A combined optical coherent tomography (OCT) pressure sensor system includes an optical cable comprising a single-mode core and a multi-mode core. An OCT optical imaging sensor near a distal end of the optical cable can be inserted into a lumen of a living being. First light exiting a distal end of the single-mode core illuminates an interior of the lumen. The OCT optical imaging sensor acquires image information about the interior of the lumen and transmits an optical signal carrying the image information into the distal end of the single-mode core, toward a proximal end of the single-mode core. An optical pressure sensor attached near the OCT optical imaging sensor receives second light from the distal end of the optical cable, senses ambient pressure within the lumen and transmits an optical signal indicative of the ambient pressure into a distal end of the multi-mode core, toward a proximal end of the multi-mode core.

24 Claims, 18 Drawing Sheets

(56) References Cited

OTHER PUBLICATIONS

"Optical coherence tomography", Wikipedia, Dec. 17, 2018, https://en.wikipedia.org/wiki/Optical_coherence_tomography, 15 pages.

R. Paschotta, "Hollow-core Fibers", Encyclopedia of Laser Physics and Technology, www.rp-photonics.com/hollow-core-fibers.html, Feb. 1, 2019, 4 pages.

R. Paschotta, "Modes", Encyclopedia of Laser Physics and Technology, www.rp-photonics.com/modes.html, Nov. 13, 2018, 7 pages.

R. Paschotta, "Fiber-optic Sensors", Encyclopedia of Laser Physics and Technology, www.rp-photonics.com/fiber_optic_sensors.html, Nov. 13, 2018, 6 pages.

R. Paschotta, "Multi-core Fibers", Encyclopedia of Laser Physics and Technology, www.rp-photonics.com/multi_core_fibers.html, Nov. 13, 2018, 5 pages.

\* cited by examiner

SYSTEMS AND METHODS OF COMBINED OPTICAL COHERENCE TOMOGRAPHY AND PRESSURE MEASUREMENT

BACKGROUND

Technical Field

The present invention relates to combined intravascular pressure measurement and imaging systems and, more particularly, to combined intravascular pressure measurement and optical coherence tomography (OCT) imaging systems that include multiple-core optical fibers for separately carrying image signals and pressure signals.

Related Art

In the medical field of blood vessel treatment, particularly in treating blood vessels with stenotic lesions or other full or partial blockages, determining an amount of blood flowing through a narrowed or stenotic region of a blood vessel can help a clinician evaluate severity of an obstruction and select an appropriate treatment. Two tools commonly used to determine the blood flow are fractional flow reserve (FFR) and optical coherence tomography (OCT).

FFR is an important functional measurement of the physiological significance of a stenosis in a blood vessel lumen. FFR involves making precise blood pressure measurements, both downstream and upstream of the stenosis, and then calculating a ratio of the downstream pressure to the upstream pressure. These blood pressure measurements are taken by inserting a pressure sensor into the blood vessel lumen, translating the pressure sensor along the lumen, between a location upstream of the stenosis and a location downstream of the stenosis, and taking pressure measurements at both locations.

FFR pressure sensors may include electrical or optical pressure transducers, and they are typically connected to their respective control circuits by respective wires or optical fibers. Optical pressure transducers have been used in recent years and have provided improved performance, accuracy, drift and ease of use, over electric pressure transducers. A typical optical pressure transducer reflects light and modulates the reflected light in relation to ambient pressure. While both single-mode fibers and multi-mode fibers can be used in FFR devices with optical pressure transducers, commercially available single-function FFR devices typically use multi-mode fibers as light conductors, due to their larger core sizes, which facilitate light gathering and pressure probe manufacture and alignment. However, a pressure sensor and its attendant electrical or optical cable inserted into a blood vessel lumen partially occlude the lumen and, consequently, affect the blood pressure measurements.

Fortunately, knowledge of lumen geometry of the blood vessel, such as inside diameter, may be used to correct for these errors in the blood pressure measurements. OCT is an important structural imaging method that can be used to provide this geometric information. OCT may be used to image the inside of the blood vessel and, in particular, to ascertain the blood vessel lumen size. OCT involves inserting an OCT probe into the blood vessel lumen, rotating the OCT probe about a longitudinal axis, translating the OCT probe along the longitudinal axis and optically imaging (by raster scanning) the inside of the blood vessel.

A single-mode optical fiber acts as a light conductor between the OCT probe and an OCT engine disposed outside a patient's body. The single-mode optical fiber provides light to illuminate the inside of the blood vessel, and the single-mode optical fiber carries an image signal back to the OCT engine. As noted, OCT may be used to determine blood vessel lumen size. In addition, OCT may be used to check stent deployment and to provide other clinically useful information.

While both OCT and FFR probes are available as separate devices, some prior art systems provide combined OCT/FFR systems. A compact combined system uses a single optical fiber core for both the OCT and FFR probes. However, because OCT involves coherent imaging, OCT typically requires a single-mode fiber. Unfortunately, single-mode fiber has a very small core diameter and often a small numerical aperture. Consequently, light reflected from only a small portion of the FFR pressure transducer can be collected by the single-mode fiber, which leads to a low signal-to-noise ratio (SNR) and requires a very meticulous, and therefore expensive, alignment process during probe manufacture. Accordingly, there is need for combined OCT/FFR systems with improved performance and low manufacturing cost.

US Pat. Publ. No. 2014/0094697 by Christopher Petroff, et al. ("Petroff"), describes current equipment and methods for treating blood vessels with stenotic lesions and other full or partial blockages. U.S. Pat. No. 8,478,384 to Joseph M. Schmitt, et al. ("Schmitt"), describes a combined OCT/pressure measurement probe and provides basic information about OCT. Wikipedia, Optical Coherence Tomography ("Wikipedia") (en.wikipedia.org/wiki/Optical_coherence_tomography) provides additional background information about OCT.

US Pat. Publ. No. US 2010/0021114 by Xin Chen, et al. ("Chen"), describes a double-clad optical fiber, such as for use with an endoscope. US Pat. Publ. No. US 2011/0205349 by Ming-Jun Li ("Li") describes a triple-clad optical fiber, such as for use with an endoscope. U.S. Pat. No. 5,077,815 by Sakae Yoshizawa, et al. ("Yoshizawa"), describes apparatus for optically connecting a single-mode optical fiber to a multi-mode optical fiber.

R. Paschotta, articles on "multi-core fibers," "fiber-optic sensors" and "modes," in the Encyclopedia of Laser Physics and Technology (collectively "Paschotta") (www.rp-photonics.com/multi_core_fibers.html, www.rp-photonics.com/fiber_optic_sensors.html and www.rp-photonics.com/modes.html), describe, respectively, multiple-core optical fibers, optical fiber transducers and light propagation modes.

The entire contents of Petroff, Schmitt, Wikipedia, Chen, Li, Yoshizawa and Paschotta are hereby incorporated by reference herein, for all purposes.

SUMMARY OF EMBODIMENTS

An embodiment of the present invention provides a combined medical sensor system. The combined medical sensor system includes an optical cable, an OCT optical imaging sensor and an optical pressure sensor. The optical cable includes both a single-mode light carrying region (core) and a multi-mode light-carrying region (core). The multi-mode light-carrying region is other than an outer-most cladding. The single-mode light-carrying region extends from a proximal end of the optical cable to a distal end of the optical cable. Similarly, the multi-mode light-carrying region extends from the proximal end of the optical cable to the distal end of the optical cable.

The OCT optical imaging sensor is attached proximate the distal end of the optical cable. The OCT optical imaging sensor is configured to be inserted into a lumen of a living being. The OCT optical imaging sensor is configured to receive first light exiting a distal end of the single-mode light-carrying region. The OCT optical imaging sensor is configured to use the first light to illuminate an interior portion of the lumen. The OCT optical imaging sensor is configured to acquire image information about the interior portion of the lumen. The OCT optical imaging sensor is also configured to transmit an optical signal carrying the image information into the distal end of the single-mode light-carrying region, toward a proximal end of the single-mode light-carrying region.

The optical pressure sensor is attached proximate the OCT optical imaging sensor. The optical pressure sensor is configured to receive second light from the distal end of the optical cable. The optical pressure sensor is configured to sense ambient pressure within the lumen. The optical pressure sensor is also configured to transmit an optical signal indicative of the ambient pressure into a distal end of the multi-mode light-carrying region, toward a proximal end of the multi-mode light-carrying region.

In any embodiment, the single-mode light-carrying region may have a first index of refraction. The multi-mode light-carrying region may have a second index of refraction. The optical cable may include a cladding diametrically outside the multi-mode light-carrying region and having a third index of refraction. The second index of refraction may be less than the first index of refraction. The third index of refraction may be less than the second index of refraction.

In any embodiment, the single-mode light-carrying region may have a first index of refraction. The multi-mode light-carrying region may have a second index of refraction. The optical cable may include a first cladding diametrically outside the multi-mode light-carrying region and having a third index of refraction. The optical cable may include a second cladding between the single-mode light-carrying region and the multi-mode light-carrying region and having a fourth index of refraction. The third index of refraction may be less than the second index of refraction. The fourth index of refraction may be less than the first index of refraction and less than the second index of refraction.

In any embodiment, the optical cable may be configured to optically isolate the single-mode light-carrying region from light in the multi-mode light-carrying region by at least 20 dB at wavelengths between about 400 nm and about 1,700 nm.

In any embodiment, the optical cable may be configured to optically isolate the single-mode light-carrying region from light in the multi-mode light-carrying region by at least 40 dB at wavelengths between about 400 nm and about 1,700 nm.

In any embodiment, the pressure sensor may be configured to receive the second light from the distal end of the single-mode light-carrying region.

In any embodiment, the combined medical sensor system may also include an optical splitter optically coupled to the distal end of the single-mode light-carrying region. The optical splitter may be configured to split light exiting the distal end of the single-mode light-carrying region between: (a) the OCT optical imaging sensor and (b) the pressure sensor.

In any embodiment, the combined medical sensor system may also include a sheath having an outside diameter. The OCT optical imaging sensor, the optical pressure sensor and the distal end of the optical cable may be disposed within the sheath. A distance between the optical splitter and a furthest reflecting surface of the pressure sensor may be less than one-half the outside diameter of the sheath.

In any embodiment, the optical splitter may include a mirror. The mirror may be configured to reflect a first portion, less than all, of the light exiting the distal end of the single-mode light-carrying region to the OCT optical imaging sensor. The mirror may be configured to also transmit a second portion, less than all, of the light exiting the distal end of the single-mode light-carrying region through the mirror to the pressure sensor.

In any embodiment, the mirror may be equally partially reflective over its entire working surface.

In any embodiment, a working surface of the mirror may be partitioned into a first region and a second region. The first region may have a first reflectivity and a first transmissivity. The first reflectivity may be greater than the first transmissivity. The first region may reflect substantially all of the first portion of the light exiting the distal end of the single-mode light-carrying region to the OCT optical imaging sensor. The second region may have a second reflectivity. The second reflectivity may be less than the first reflectivity. The second region may also have a second transmissivity. The second transmissivity may be greater than the first transmissivity. The second transmissivity may be greater than the second reflectivity. The second region may transmit substantially all of the second portion of the light exiting the distal end of the single-mode light-carrying region through the mirror to the pressure sensor.

In any embodiment, the combined medical sensor system may also include a single light source. The single light source may be optically coupled to the proximate end of the single-mode light-carrying region. The single light source may be configured to thereby provide the first light to the OCT optical imaging sensor and the second light to the pressure sensor.

In any embodiment, the combined medical sensor system may also include a first light source. The combined medical sensor system may also include a second light source, distinct from the first light source. The first light source may be optically coupled to the proximate end of the single-mode light-carrying region. The first light source may be configured to thereby provide the first light to the OCT optical imaging sensor. The second light source may be optically coupled to the proximate end of the single-mode light-carrying region. The second light source may be configured to thereby provide the second light to the pressure sensor.

In any embodiment, the combined medical sensor system may also include a light source optically coupled to the proximate end of the single-mode light-carrying region. The light source may be configured to thereby provide the first light to the OCT optical imaging sensor. The combined medical sensor system may also include an optical mode converter. The optical mode converter may be optically coupled between the light source and the proximate end of the single-mode light-carrying region. The optical mode converter may be configured to thereby provide multi-mode light to the pressure sensor.

In any embodiment, the optical mode converter may include a polarization scrambler.

In any embodiment, the combined medical sensor system may also include a light source optically coupled to the proximate end of the single-mode light-carrying region. The light source may be configured to thereby provide the first light to the OCT optical imaging sensor and the second light to the pressure sensor. The first light may include a first range of wavelengths. The second light may include a second range of wavelengths that does not overlap with the first range of wavelengths. An optical filter may be optically coupled between: (a) the distal end of the single-mode light-carrying region and (b) the pressure sensor. The optical filter may be configured to: (i) transmit the second range of wavelengths of light to the pressure sensor with a transmissivity of at least about 90% and (ii) transmit the first range of wavelengths of light to the pressure sensor with a transmissivity of at most about 10%.

In any embodiment, the light source may include a first light source and a second light source. The second light source may be distinct from the first light source. The first light source may be configured to provide the first light. The second light source may be configured to provide the second light.

In any embodiment, the pressure sensor may be configured to receive the second light from the distal end of the multi-mode light-carrying region.

In any embodiment, the combined medical sensor system may also include an optical coherence tomography engine and a pressure measurement engine. The optical coherence tomography engine may be optically coupled to the proximal end of the single-mode light-carrying region. The optical coherence tomography engine may be configured to receive the signal carrying the image information and generate an image therefrom. The pressure measurement engine may be optically coupled to the proximal end of the multi-mode light-carrying region. The pressure measurement engine may be configured to receive the optical signal indicative of the ambient pressure and estimate the ambient pressure therefrom.

In any embodiment, the combined medical sensor system may also include a first optical connector, a second optical connector and a switch. The first optical connector may be configured to be disconnectably optically coupled to the proximal end of the optical cable. The second optical connector configured to be disconnectably optically coupled to the proximal end of the optical cable. The switch may have at least a first position and a second position. The proximal end of the optical cable may be configured to be selectively disconnectably optically coupled to at most one at a time of the first optical connector and the second optical connector. The optical coherence tomography engine and the pressure measurement engine may have a common optical input port. The switch may be optically coupled between the first optical connector, the second optical connector and the common optical input port such that, in the first position, the switch optically couples the first optical connector to the common optical input port and, in the second position, the switch optically couples the second optical connector to the common optical input port.

In any embodiment, the multi-mode light-carrying region may include a plurality of multi-mode light carrying sub-regions. The single-mode light-carrying region may be isolated from light in each multi-mode light-carrying sub-region by at least 10 dB at wavelengths between about 400 nm and about 1,700 nm.

In any embodiment, the plurality of multi-mode light carrying sub-regions may be concentric with the single-mode light-carrying region.

In any embodiment, the multi-mode light-carrying region may have a numerical aperture greater than about 0.05.

In any embodiment, the multi-mode light-carrying region may have a numerical aperture between about 0.05 and about 0.5. The single-mode light-carrying region may have a numerical aperture between about 0.05 and about 0.2.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
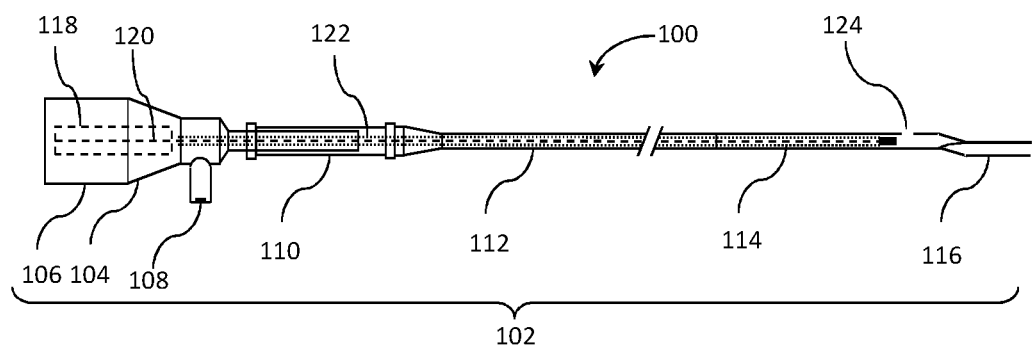
FIG. 1 is a side view of an exemplary combined OCT/pressure probe, according to an embodiment of the present invention.

As used herein, unless otherwise indicated, the following terms shall have the following definitions:

Core—A core, also referred to herein as a "light-carrying region" or a "light guiding region," of an optical fiber is a continuous longitudinal, optically transparent (at wavelengths of interest), region in the optical fiber, extending from one end of the optical fiber to the other end. The core may be made of a material, such as glass or plastic, or the core may be hollow. Although cylindrical cores having circular cross sections disposed co-axially with the optical fiber are common, other cross-sectional shapes, and non-co-axial placements, may be used. The core is surrounded by a medium having a lower index of refraction than the core, typically a cladding of a different glass or plastic. Light travelling in the core reflects from the core-cladding boundary due to total internal reflection, as long as the angle between the light and the boundary is less than the critical angle. As a result, the optical fiber transmits essentially all rays that enter the fiber with a sufficiently small angle to the fiber's axis. The limiting angle is called an acceptance angle, and the rays that are confined by the core-cladding boundary are called guided rays. An optical cable includes one or more cores.

Multiple-core—A multiple-core optical fiber cable includes at least two independent cores. The cores may be optically isolated from each other to prevent cross-talk, at least to a specified degree of isolation, at a specified range of wavelengths, and/or in a specified direction. In some cases, a core is optically isolated to prevent light entering the core from another core or from a cladding, but not necessarily to prevent light from the core entering the other core or cladding. For example, a single-mode core may be isolated from a multi-mode core to prevent light from the multi-mode core entering the single-mode core. In other words, the isolation may be one-way or the isolation may be greater in one direction than in the opposite direction.

Cladding—Cladding, also referred to herein as an "isolation region," in an optical fiber is one or more layers of materials, typically of lower refractive index, compared to a core, in intimate contact with the core. As noted, the cladding causes light to be confined to the core by total internal reflection at the boundary between the core and the cladding. Light propagation in the cladding is suppressed in typical fiber. Although some known optical fibers support cladding propagation modes, as used herein cladding is not used to propagate light.

Single-mode—A single-mode optical fiber (SMF) is an optical fiber, or the core of an optical fiber, designed to carry light only directly down the core, i.e., in the transverse mode. Modes are possible solutions of the Helmholtz equation for waves, which is obtained by combining Maxwell's equations and boundary conditions. Modes define the ways waves travel through space, i.e., how each wave is distributed in space. Multiple waves can have the same mode but have different frequencies (wavelengths).

Multi-mode—A multi-mode optical fiber (MMF) is an optical fiber, or the core of an optical fiber, designed to simultaneously carry multiple modes of light. A multi-mode fiber or core typically has a relatively large core diameter, compared to an otherwise comparable single-mode optical fiber or core, that enables multiple light modes to propagate therealong.

Embodiments of the present invention provide combined optical pressure and OCT medical imaging sensor systems, including combined optical pressure/OCT measurement probes. These systems feature high signal-to-noise ratios in their pressure channels, without requiring the meticulous and expensive alignment processes during manufacture that plague prior art combined pressure/OCT probes.

Each such system includes both an optical pressure measurement transducer and an OCT optical imaging sensor on a common catheter. The catheter includes a multiple-core optical cable. One core of the multiple-core optical cable is a single-mode core, and another core of the multiple-core optical cable is a multi-mode core. The single-mode core is used to carry light to the OCT optical imaging sensor, i.e., to illuminate an interior of a blood vessel, and to carry an optical signal with image information back to an OCT engine, which is configured to receive the signal carrying the image information and generate an image from the optical signal from the OCT optical imaging sensor.

Either the single-mode core or the multi-mode core carries light to the optical pressure measurement transducer. The optical pressure measurement transducer senses ambient pressure within the blood vessel and transmits an optical signal indicative of the ambient pressure. The optical signal indicative of the ambient pressure may be carried by the single-mode core or by the multi-mode core to a pressure measurement engine, which is configured to receive the optical signal indicative of the ambient pressure and estimate the ambient pressure from the optical signal from the optical pressure measurement transducer.

The multi-mode core may have a large numerical aperture, and thus may capture more light from the optical pressure measurement transducer, than a single-mode core could capture. The single-mode core may be optically isolated, so as not to receive light from the multi-mode core to prevent cross-talk between the optical signal carrying the OCT image information and the optical signal carrying the optical pressure measurement information. Some embodiments include a cladding between the single-mode core and the multi-mode core to provide this optical isolation. Stepped or continuous optical indexes of the cores and the cladding may be used to create this optical isolation.

FIG. 1 is a side view of an exemplary combined OCT/pressure probe 100, according to an embodiment of the present invention. The probe 100 is in the form of a catheter 102 for easy insertion into a blood vessel of a patient. As viewed in FIG. 1, the left end of the catheter 102 is referred to as the proximal end of the catheter 102, and the right end is referred to as the distal end of the catheter 102. Disposed within the probe's outside housing 104 are a proximal connector 106 and a liquid purge port 108. A telescoping section 110 is mechanically coupled to the outside housing 104. A proximal sheath 112 extends from the telescoping section 110 to a distal sheath 114 and a rapid-exchange section 116. Inside the housing 104 are rotary inner parts, including an optical connector 118, a multiple-core optical fiber cable 120 and a torque transmission coil 122. At least one opening 124 allows the combined OCT/pressure probe 100 to sense pressure in the blood vessel.

Figure 2:
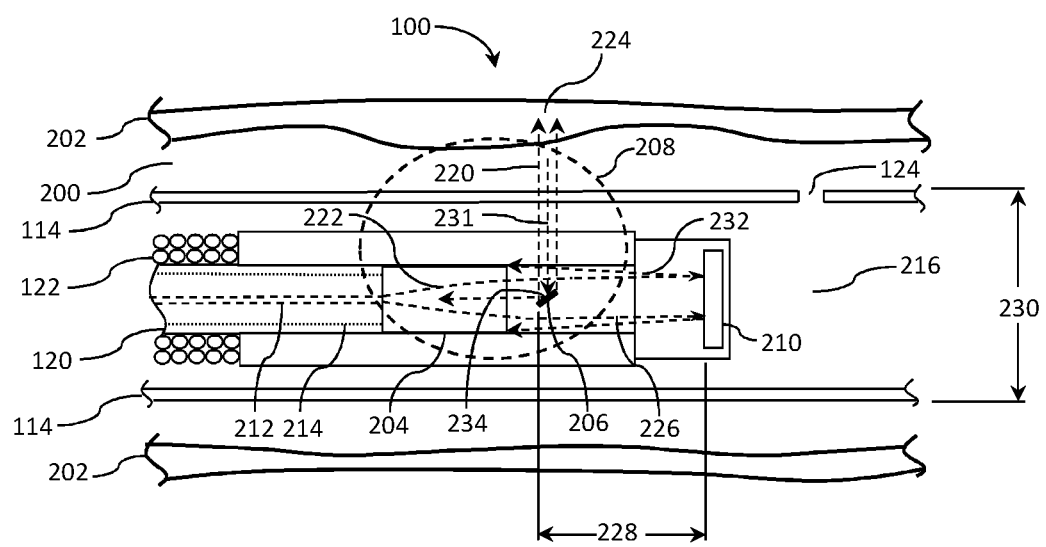
FIG. 2 is an enlarged, cut-away view of a portion of the exemplary combined OCT/pressure probe of FIG. 1, according to an embodiment of the present invention.

FIG. 2 shows an enlarged, cut-away view of a distal portion of the probe 100 disposed within a lumen 200 of a vessel 202, such as a blood vessel. The vessel 202 may be filled with blood or other liquid. Disposed within the distal portion of the probe 100 are an optical lens 204, an optical beam splitter 206, such as a partially-reflective mirror, an OCT imaging sensor 208 and a pressure sensing transducer 210. The multiple-core optical fiber cable 120 has a proximal end and a distal end, which correspond, respectively, to the proximal and distal ends of the catheter 102.

The multiple-core optical fiber cable 120 is used for transmitting and collecting light for both OCT imaging and pressure measurement. Specifically, the multiple-core optical fiber cable 120 includes both a single-mode core 212 and at least one multi-mode core 214. The single-mode core 212 is used for transmitting OCT signals, while the pressure signals are transmit through either the multi-mode core 214 or the single-mode core 212, depending on the embodiment. The single-mode core 212 has a proximal end and a distal end that correspond, respectively, to the proximal and distal ends of the multiple-core optical fiber cable 120. Similarly, the multi-mode core 214 has a proximal end and a distal end that correspond, respectively, to the proximal and distal ends of the multiple-core optical fiber cable 120.

The probe 100 is configured to be placed inside the vessel. In some embodiments, the probe 100 utilizes the multiple-core optical fiber cable 120 for transmitting both single-mode light for OCT imaging and single-mode or multi-mode light for pressure measurement.

In one embodiment, the probe sheaths 112 and 114 collectively define a bore 216, and the distal sheath 114 defines the at least one opening 124 to an environment (the lumen 200) in the vessel 202, allowing ambient pressure in the environment to be transmitted to the bore 216. The optical lens 204 is disposed inside the bore 216 and in optical communication with the multiple-core optical fiber cable 120. The optical pressure transducer 210 is also disposed inside the bore 216 and is in optical communication with the multiple-core optical fiber cable 120 via the lens 204. In some embodiments, the optical beam splitter 206 is disposed and configured to direct a portion 220, less than all, of light 222 exiting the multiple-core optical fiber cable 120 toward an OCT imaging target 224, for example a portion of a wall of the blood vessel 202. The optical beam splitter 206 directs another portion 226, less than all, of the light 222 exiting the multiple-core optical fiber cable 120 to the optical pressure transducer 210 to excite the pressure transducer 210. In some embodiments, a distance 228 between the optical beam splitter 206 and the pressure sensor 210 is less than one-half the outside diameter 230 of the distal sheath 114

In some embodiments, light for the OCT imaging sensor 208 is supplied by the single-mode core 212, and the excitation light 226 for the pressure transducer 210 is supplied by the multi-mode core 214. In other embodiments, light for both the OCT imaging sensor 208 and the pressure transducer 210 is supplied by the single-mode core 212.

In one embodiment, light for OCT imaging exits the distal end of the single-mode core 212 and is focused by the lens assembly 204. As noted, part of the light 222 is reflected by a partially reflective surface of the optical beam splitter 206 out of the probe 100, from the side, toward the imaging target 224. Since the surface of the optical beam splitter 206 is partially reflective and partially transmissive, the surface may intersect the entire beam 222 of light from the multiple-core optical fiber 120. Alternatively, a fully-reflective mirror that is smaller than the light beam 222 may be used.

Light returning 231 from the imaging target 224 is collected and returned to the single-mode core 212 for subsequent analysis by an OCT engine. Because the optical beam splitter 206 is only partially reflective, light for the pressure transducer 210 exiting the multi-mode core 214 passes through the lens assembly 204 and is then transmitted through the optical beam splitter 206 to the optical pressure transducer 210. Light 232 returning from the pressure transducer 210 returns to the multi-mode core 214 of the multiple-core optical fiber cable 120 for pressure measurement. The multi-mode core 214 has a cross-sectional area larger than the single-mode core 212. Therefore, advantageously, the light 232 returning from the pressure transducer 210 is collected with a higher collection efficiency by the multi-mode core 214 than would be possible with the single-mode core 212. This higher efficiency facilitates both system implementation and probe manufacturing.

In another embodiment, the light path for the OCT is the same as above. However, the excitation light 226 for the pressure transducer 210 is supplied by the single-mode core 212. The excitation light 226 for the pressure transducer 210 exits the single-mode core 212 and passes through the lens assembly 204 and the partially reflective optical beam splitter 206, to the optical pressure transducer 210. The light 232 returning from the pressure transducer 210 returns to the multi-mode core 214 of the multiple-core optical fiber cable 120 and is subsequently analyzed for pressure measurement. This single-mode excitation and multi-mode collection is useful when, for example, the excitation source is a single-mode source.

The optical beam splitter 206 is important for performance of the probe 100. Ideally, all the OCT light 220 should be reflected to the imaging target 224, while all of the pressure measurement light 226 should be transmitted to the pressure transducer 210. This split of the light from the multiple-core optical fiber cable 120 may be achieved in any of several ways. One way to achieve this split is by using different wavelength bands for OCT and pressure measurement and a wavelength-selective filter. For example, in one embodiment, the OCT light 220 is in the 1200-1400 nm band, and the pressure measurement light 226 is in the 700-900 nm band. In this embodiment, a dichroic coating 234 on the optical beam splitter 206 redirects or passes each wavelength band toward its respective intended target. Other multiplexing methods include polarization dependent multiplexing, etc.

The dichroic selective reflective coating 234 may be difficult or costly to achieve. Furthermore, sometimes it is desirable to use the same wavelength(s) of light to excite both the OCT imaging and the pressure measurement. In such cases, a partial reflective, but not wavelength selective, coating may be used as the reflective/transmissive coating. In this embodiment, the partially reflective coating is evenly applied to the entire working surface of the optical beam splitter 206 mirror, and the mirror is as large as the light beam 222. In other words, the mirror is equally partially reflective over its entire working surface. Because the OCT imaging usually requires higher optical power than the pressure measurement, the coating should reflect more than half of the light, preferably more than 90% of the light, toward the imaging target 224 and transmit less than half of the light 222, preferably less than 10% of the light 222, toward the pressure transducer 210.

Figure 3:
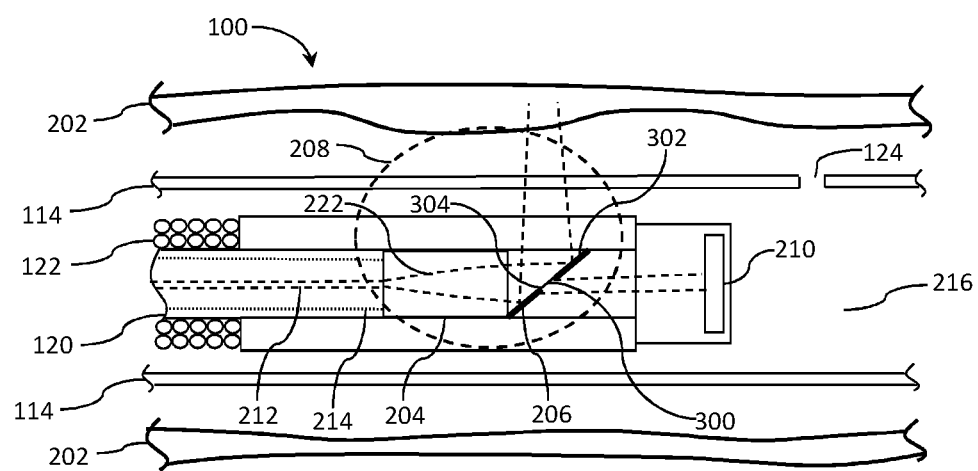
FIG. 3 is an enlarged cut-away view of a portion of the exemplary combined OCT/pressure probe of FIG. 1, according to another embodiment of the present invention.

FIG. 3 shows another embodiment for splitting the excitation light. In this embodiment, the optical beam splitter 206 defines an aperture 300 in the working surface of the optical beam splitter 206 mirror. The aperture 300 partitions the working surface of the mirror into two distinct regions. The first region 302 is more reflective than it is transmissive, and the second region 304 is more transmissive than it is reflective. For example, the aperture 300 may be implemented as a hole in a mirror, or as a mirror that is smaller, as viewed from the multiple-core optical fiber cable 120, than the light beam 222 in which the mirror is disposed. Alternatively, the two regions 302 and 304 may be implemented with two different coatings, or different thicknesses of the same type of coating, such that the coatings on the two regions 302 and 304 have different respective reflectivities and transmissivities.

The first region 302 has a first reflectivity and a first transmissivity. The first reflectivity is greater than the first transmissivity. Consequently, the first region 302 reflects substantially all of the light exiting the distal end of the single-mode light-carrying core 212 that reaches the OCT optical imaging sensor 208.

The second region 304 has a second reflectivity and a second transmissivity. As noted, the second region 304 is more transmissive than it is reflective. Thus, the second transmissivity is greater than the second reflectivity. The second region 304 is less reflective, and more transmissive, than the first region 302. Thus, the second reflectivity of the second region 304 is less than the first reflectivity of the first region 302, and the second transmissivity of the second region 304 is greater than the first transmissivity of the first region 302. Consequently, the second region 302 transmits substantially all of the light exiting the distal end of the single-mode core 212 that reaches the pressure sensor 210.

Figure 4:
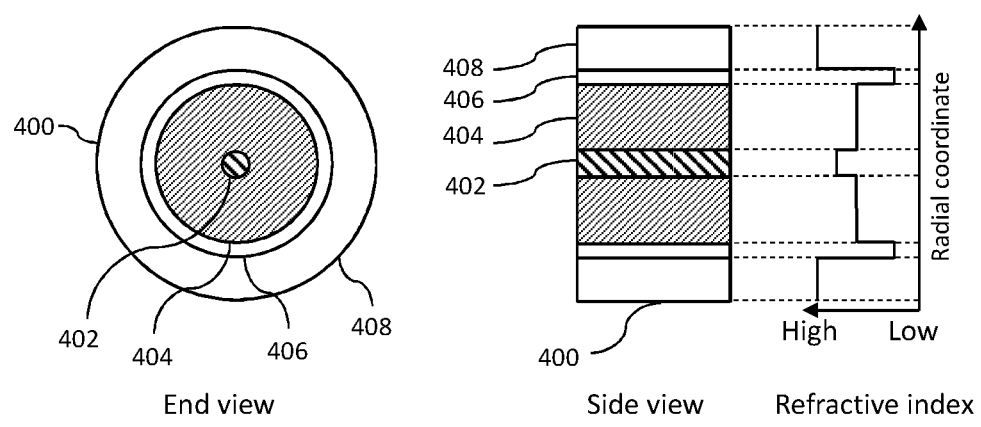
FIG. 4 is a cross-sectional view (left) and a graph of index of refraction versus radius (right) of a multiple-core optical cable used in either of the combined OCT/pressure probes of FIGS. 1-3, according to an embodiment of the present invention.

FIG. 4 shows an exemplary cross-sectional view (left) and corresponding refractive index profile diagram (right) of a multiple-core optical fiber cable 400 that could be used as the multiple-core optical fiber cable 120 in the combination OCT/pressure probe 100 discussed herein. The refractive index profile (right) is designed so the multiple-core optical fiber cable 400 has a central single-mode core 402 and a surrounding multi-mode core 404. Diametrically outside the multi-mode core 404 is a layer of low-index outer cladding 406, and outside the cladding 406 is a high-index buffer layer 408. The buffer layer 408 is a protection layer for the fiber. The buffer layer 408 is often made of material having a large attenuation coefficient. All or part of the buffer layer 408 is often stripped away at connection points to ensure the buffer layer 408 does not carry any light.

The refractive index profile (right) is characterized in that the index of refraction of the multi-mode core 404 is less than the index of refraction of the single-mode core 402, and the index of refraction of the cladding 406 is less than the index of refraction of the multi-mode core 404.

OCT light is carried by the central single-mode core 402, while the pressure measurement light is carried by the single-mode core 402 and/or the multi-mode core 404, as discussed herein. Because there are two cores 402 and 404 in this multiple-core optical fiber cable 400, it is sometimes referred as double-core fiber. Within each layer, the refractive index can be either homogeneous or graded, and both are within the scope of this invention.

Figure 5:
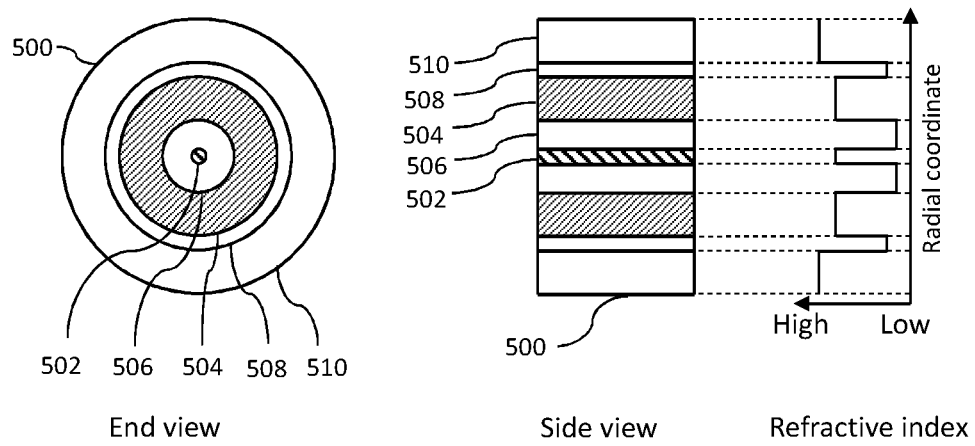
FIG. 5 is a cross-sectional view (left) and a graph of index of refraction versus radius (right) of a multiple-core optical cable used in either of the combined OCT/pressure probes of FIGS. 1-3, according to another embodiment of the present invention.

FIG. 5 shows an exemplary cross-sectional-view (left) and corresponding refractive index profile diagram (right) of a multiple-core optical fiber cable 500 that could be used as the multiple-core optical fiber cable 120 in the combination OCT/pressure probe 100 discussed herein. The multiple-core optical fiber cable 500 advantageously reduces cross-talk between a single-mode core 502 and a multi-mode core 504 by disposing a low-index region 506 diametrically between the single-mode core 502 and the multi-mode core 504.

In the prior art, when referring to optical fiber cables with more than two layers or three regions, the terms "core" and "cladding" are often used interchangeably for intermediate layers. To avoid confusion among different layers in multiple-core optical fiber cable, as used herein, an innermost layer is called an inner core, for example single-mode core 502 is an inner core. Counting outward from the inner core, the layers are subsequently called: an inner cladding (corresponding to the low-index region 506), an outer core (corresponding to the multi-mode core 504), an outer cladding (corresponding to a cladding 508), and a buffer (corresponding to a buffer 510).

Indexes of refraction of the inner core (single-mode core 502), inner cladding (low-index region 506), outer core (multi-mode core 504), outer cladding (cladding 508) and buffer (buffer 540) are n0, n1, n2, n3 and n4, respectively. In this embodiment, n0>n1, n0>n3, n2>n1, n2>n3 and n4 is greater than any of the other layers. To further increase the collection efficiency of the multi-mode core 504, the index of the outer core (multi-mode core 504) is preferably larger than the index of the inner core, i.e., n2>n0 (not shown in FIG. 5). In addition, the index of the outer cladding 508 is preferably larger than or equal to that of the first inner cladding (low-index region 506), i.e., n3>n1. This is to guarantee the light is not guided by the first inner cladding (low-index region 506). Within each layer, the refractive index can be either homogeneous or graded, and both are within the scope of this invention. The buffer 510 is a protection layer for the fiber. It is often made of material having a large attenuation coefficient and a higher refractive index to ensure it is not light-guiding. By separating the light-guiding cores 502 and 504 by the low-index region 506, cross-talking between the cores 502 and 504 is reduced, resulting in better OCT imaging and pressure measurement.

The above-described multiple-core optical fiber cables 400 and 500 are just examples. Other suitable configurations of multiple-core optical fiber cable are acceptable. For example, FIGS. 6-8 show cross-sectional diagrams of other exemplary multiple-core optical fiber cables (MCF) that could be used for the multiple-core optical fiber cable 120 in the combination OCT/pressure probe 100.

Figure 6:
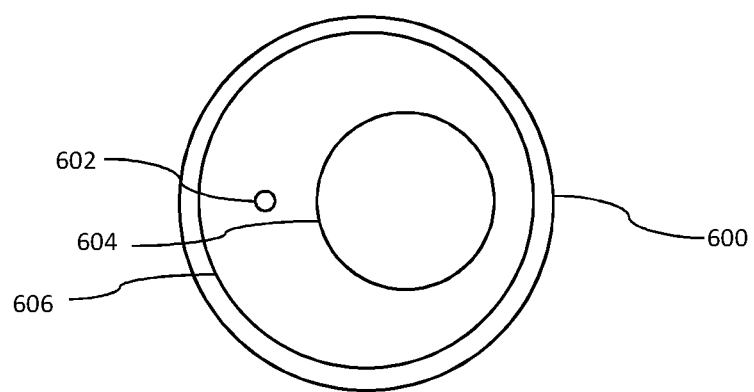
FIGS. 6-8 are cross-sectional views of respective multiple-core optical cables used in any of the combined OCT/pressure probes of FIGS. 1-3, according to respective alternative embodiments of the present invention.

FIG. 6 shows a non-concentric MCF 600. The cores 602 and 604 are not concentric. As with the MCFs 400 and 500, a cladding 606 of lower refractive index is disposed between the cores 602 and 604. Some of the cores 602 and 604, such as the core 602, may be designed to be single-mode cores and can be used for OCT, while other cores, such as the core 604, may be designed to be multi-mode cores to have high receiving efficiency.

Figure 7:
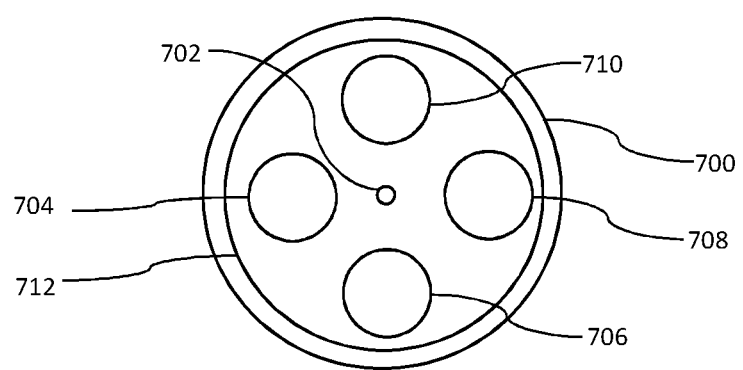

FIG. 7 shows another design of a MCF 700. Cores 702, 704, 706, 708 and 710 are separated from each other by cladding 712 of lower refractive index. The central core 702 may be designed to be a single-mode core, while some or all of the other cores 704-710 may be designed to be multi-mode cores. It should be noted that the cores 704-710 are not necessarily the same in cross-sectional size or shape. In some cases, non-circular cores and/or claddings may offer advantages. For example, because light emitting areas of most laser diode are rectangular, rectangular cross-sectioned fiber geometries offer an effective way to couple laser diode light into the fiber, because the contact area between the light emitting area and the end of the fiber is optimized to match one another. Another example where non-circular cores are useful is when polarization-related information is used in OCT or pressure measurement. Non-circular claddings can be used to maintain polarization as light propagates through the core.

Figure 8:
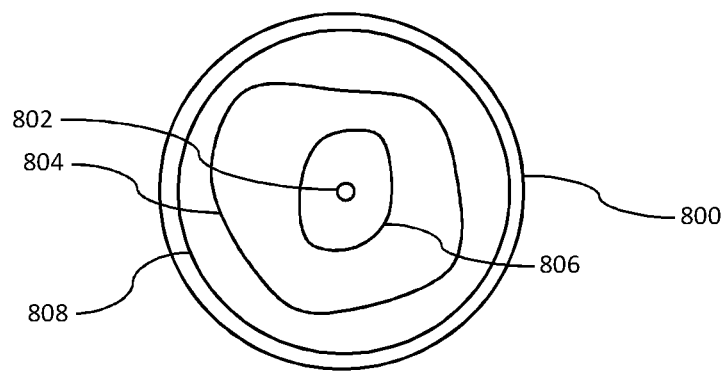

FIG. 8 shows an example of an MCF 800 that has cores 802 and 804 and a cladding 806 of arbitrary shape. The MCF 800 also has another cladding 808. The examples in FIG. 6-8 describe variations of the embodiment, but they should not be considered scope-limiting.

FIGS. 9-18 are schematic diagrams of respective combined OCT/pressure measurement systems that include either of the combined OCT/pressure probes of FIGS. 1-3, any of the multiple-core optical fiber cables of FIGS. 4-8, corresponding OCT engines, corresponding pressure measurement engines and optical interconnection components, according to respective embodiments of the present invention.

Figure 9:
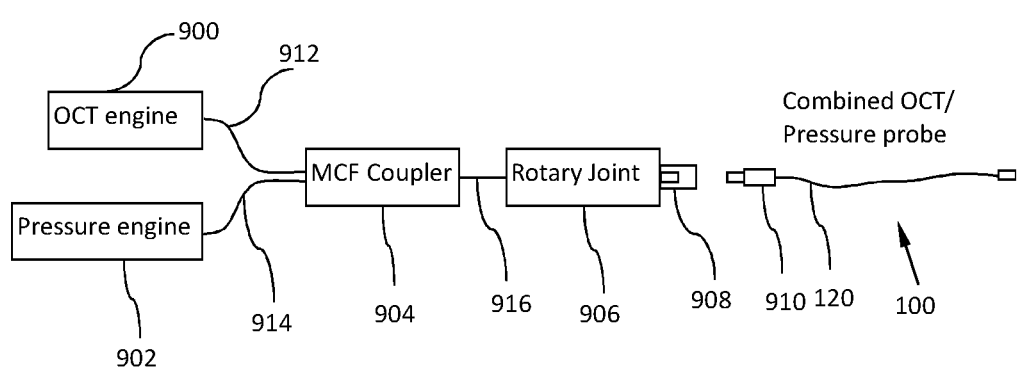
FIG. 9 is a schematic diagram of a combined OCT/pressure measurement system that includes either of the combined OCT/pressure probes of FIGS. 1-3, any of the multiple-core optical fiber cables of FIGS. 4-8, a corresponding OCT engine, a corresponding pressure measurement engine and optical interconnection components, according to an embodiment of the present invention.

FIG. 9 shows a system that is suitable for OCT and pressure measurement in connection with the combination OCT/pressure probe 100. The system includes an OCT engine 900, a pressure engine 902, a multiple-core optical fiber cable (MCF) coupler 904, a MCF rotary joint 906, an MCF connector 908, the combined OCT/pressure probe 100 with a MCF connector 910 at the proximal end of its MCF 120. A sample arm of the OCT engine 900 is optically connected to the MCF coupler 904, preferably through a single-mode fiber 912. The optical pressure engine 902 is based on multi-mode light sensing and is connected to the MCF coupler 904, preferably through a multi-mode fiber 914. Single-mode light and multi-mode light, such as from the OCT engine 900 and the pressure engine 902 or another source (not shown), are coupled to a single-mode core and a multi-mode core, respectively, of a MCF 916 through the MCF coupler 904. Both the single-mode light and the multi-mode light propagate through the optical rotary joint 906 to the combined OCT/pressure probe 100, passing through the MCF connectors 908 and 910. The rotary joint 906 is able to couple the single-mode core and multi-mode core of the MCF 916 to the single-mode core and the multi-mode core, respectively, of another MCF. OCT light returning from the probe 100 propagates through the rotary joint 906, the MCF coupler 904 and the single-mode fiber 912, after which it is collected by the OCT engine 900. Light returning from the pressure transducer returning from the probe 100 propagates through the rotary joint 906, the MCF coupler 904 and the multi-mode fiber 914, after which it is collected by the pressure measurement engine 902.

Figure 10:
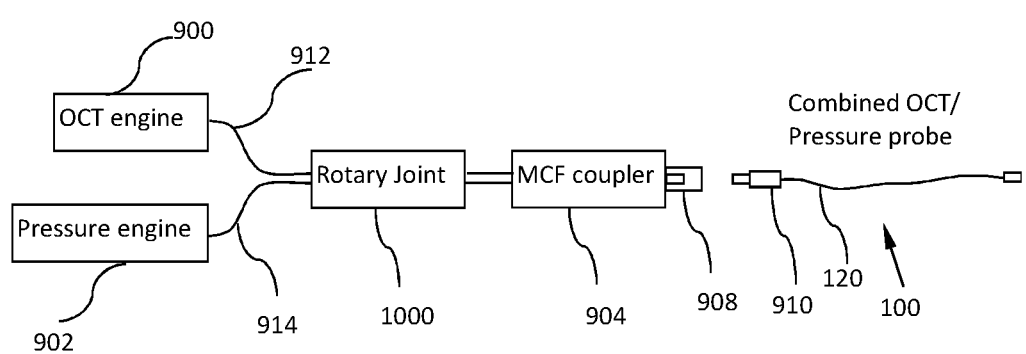
FIGS. 10-18 are schematic diagrams of respective combined OCT/pressure measurement systems that include either of the combined OCT/pressure probes of FIGS. 1-3, any of the multiple-core optical fiber cables of FIGS. 4-8, corresponding OCT engines, corresponding pressure measurement engines and optical interconnection components, according to respective alternative embodiments of the present invention.

It is sometimes difficult to make a rotary joint that couples both the single-mode core and the multi-mode core of an MCF to the single-mode core and the multi-mode core of another MCF, with high coupling efficiency, low cross-talk and high rotational speed. FIG. 10 shows another system that is suitable for OCT and pressure measurement in connection with the combination OCT/pressure probe 100 that solves this problem. The system includes an OCT engine 900, a pressure engine 902, a two-channel fiber-optic rotary joint 1000, an MCF coupler 904, an MCF connector 908 and a combined OCT/pressure probe 100. Most of the components of the system are similar to those in FIG. 9, respectively. The working principles are also similar. However, the positions of the rotary joint 1000 and the MCF coupler 904 are switched. This system requires a two-channel fiber-optic rotary joint 1000 that has both a single-mode channel and a multi-mode channel. During rotary imaging by the probe 100, both the MCF coupler 904 and some parts of the probe 100 rotate.

Figure 11:
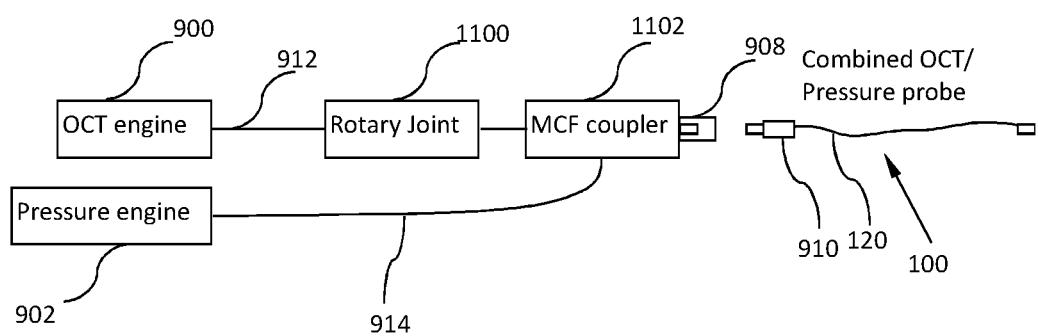

FIG. 11 shows another system that is suitable for OCT and pressure measurement in connection with the combination OCT/pressure probe 100. The system includes an OCT engine 900, a pressure engine 902, a single-channel fiber-optic rotary joint 1100, an MCF coupler 1102, an MCF connector 908, and the combined OCT/pressure probe 100. The OCT engine 900, the pressure engine 902, and the combined OCT/pressure probe 100 are similar to those in FIG. 9. However, the system needs only a one-channel single-mode fiber optic rotary joint 1100. The MCF coupler 1102 is a hybrid type that is able to couple a rotary single-mode light channel and a stationary (non-rotating) multi-mode light channel with the single-mode core and the multi-mode core, respectively, of a rotating MCF.

Figure 12:
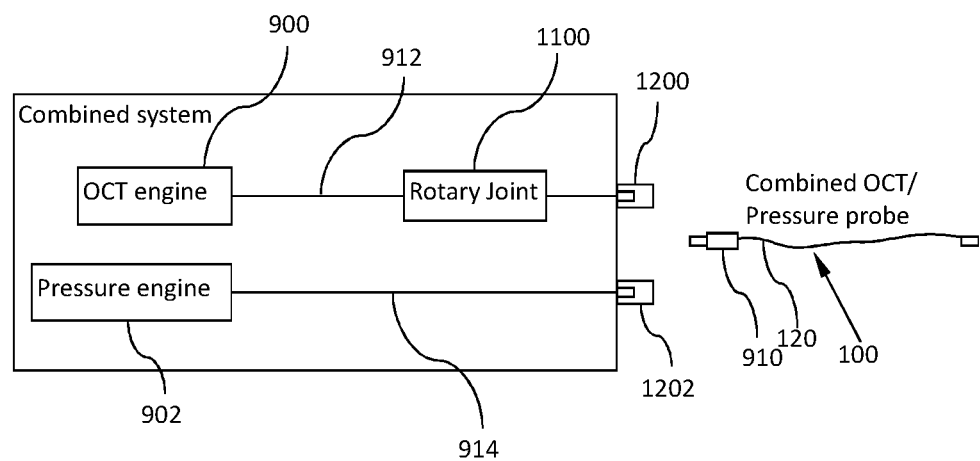

FIG. 12 shows yet another exemplary system that is suitable for OCT and pressure measurement in connection with the combination OCT/pressure probe 100. The system includes an OCT engine 900, a pressure engine 902, a single-channel fiber-optic rotary joint 1100, a single-mode connector 1200, a multi-mode connector 1202 and the combined OCT/pressure probe 100. Each of the single-mode connector 1200 and the multi-mode connector 1202 is configured to receive (mate with) the MCF connector 910, although the single-mode connector 1200 optically couples with only the single-mode channel of the MCF connector 910, and the multi-mode connector 1202 optically couples with only the multi-mode channel of the MCF connector 910.

The OCT engine 900, the pressure engine 902 and the combined OCT/pressure probe 100 are similar to those in the FIG. 9. The fiber-optic rotary joint 1100 is similar to that in the FIG. 11. However, the system of FIG. 12 includes two subsystems (OCT and pressure), and the combined OCT/pressure probe 100 can be connected to only one of the two subsystems at a time, depending on which connector 1200 or 1202 the combined OCT/pressure probe 100 is connected to. The OCT subsystem uses single-mode fiber 912 and makes a single-mode connection, via the connectors 1200 and 910, to the combined probe 100. Imaging light propagates through the single-mode core of the MCF 120 in the combined probe 100. The pressure measurement subsystem uses multi-mode fiber 914 and makes a multi-mode connection, via the connectors 1202 and 910, to the combined probe 100. Light propagates mostly or exclusively in the multi-mode core(s) of the MCF 120. The advantages of this configuration include reduced crosstalk between OCT and pressure measurements and elimination of an MCF coupler. A user can still acquire OCT images and pressure measurements with one probe 100 by switching the combined probe 100 between the connectors 1200 and 1202.

Figure 13:
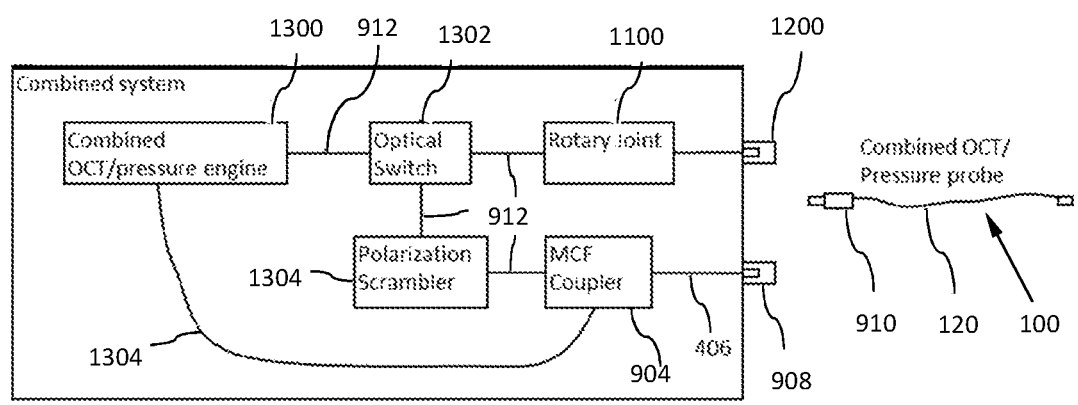

The systems shown in FIGS. 9-12 typically use separate light sources to excite the OCT imaging sensor 208 and the pressure transducer 210. FIG. 13 shows another exemplary system that uses one single-mode light source to excite both the OCT imaging sensor 208 and the pressure transducer 210 to reduce cost. The system includes a combined OCT/pressure engine 1300, an optical switch 1302, a fiber-optic rotary joint 1100, a single-mode connector 1200, a polarization scrambler 1304, an MCF coupler 904, a MCF connector 908 and the combined OCT/pressure probe 100. The combined OCT/pressure engine 1300 is a combination of the OCT engine 900 and the pressure engine 902 described above, with respect to FIG. 9, except that the combined OCT/pressure engine 1300 contains only one light source, which has single-mode output. While OCT measurements are acquired, the optical switch 1302 directs the light towards the fiber-optic rotary joint 1100. Single-mode light for OCT imaging propagates in the single-mode core 212 (FIG. 2) of the MCF 120 in the probe 100. However, when pressure measurements are acquired, the optical switch 1302 directs the light towards the MCF coupler 904.

The single-mode excitation light is transmitted towards the pressure transducer in the single-mode core 212 (FIG. 2). However, the collected pressure signal propagates along the multi-mode core 214 (FIG. 2) to the MCF coupler 904. The return signal from the pressure transducer 210 is then split into a multi-mode arm 1304 of the MCF coupler 904. The polarization scrambler 1304 can be used between the optical switch 1302 and the MCF coupler 904 to cancel out error caused by the polarization effect.

Figure 14:
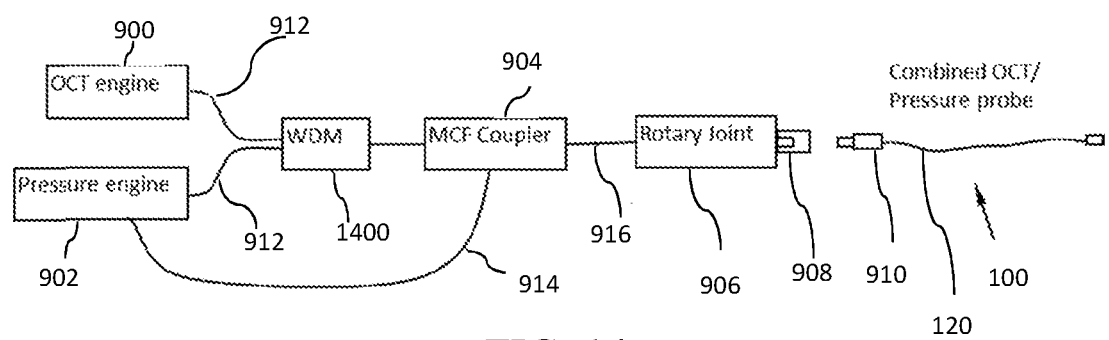

FIG. 14 shows an exemplary system that uses single-mode light to excite both the OCT imaging sensor 208 and the pressure transducer 210. However, a different wavelength band is used to excite the OCT imaging sensor 208 from the band used to excite the pressure transducer 210. The system is similar to the system shown in FIG. 9, with the addition of a wavelength division multiplexer (WDM) 1400. The WDM 1400 combines the two wavelengths (excitation signals) from the OCT engine 900 and the pressure engine 902 into the single-mode input of the MCF coupler 904. While the excitation wavelengths for pressure measurement are transmitted towards the combined probe 100 in single-mode, the return pressure signal is collected in multi-mode and is transmitted back to the MCF coupler 904. The multi-mode light from MCF 916 is then directed to the multi-mode fiber 914 and the pressure engine 902. This configuration allows use of single-mode light sources with different wavelengths for the OCT and pressure measurements. The crosstalk between the two modalities can be greatly reduced.

Figure 15:
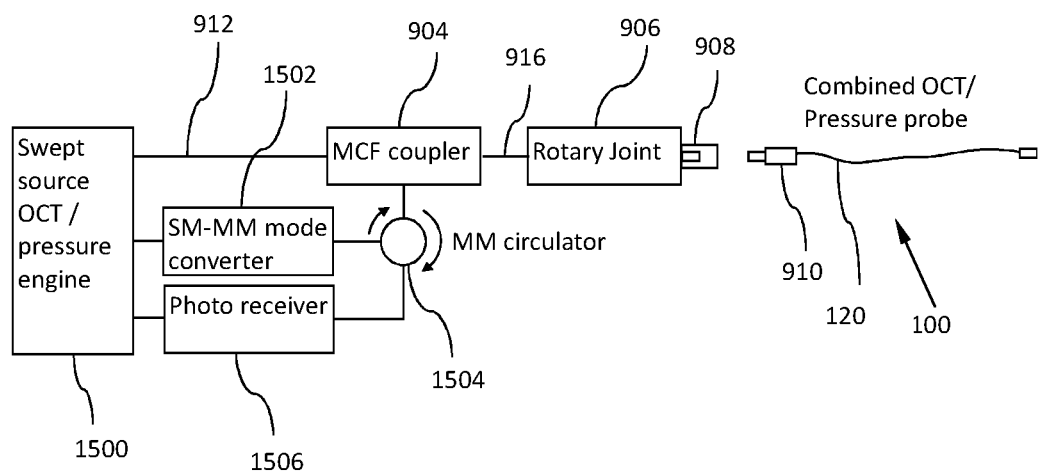

For OCT systems that use Fourier domain OCT (FD-OCT) techniques, because the optical frequency information is available through a built-in spectrometer or a swept source, it is possible to simplify the combined OCT/pressure measurement system to save cost. FIG. 15 shows an exemplary combination OCT/pressure measurement system that incorporates an FD-OCT system that uses a swept source. To illustrate this arrangement, without loss of generality, the MCF coupler 904 and the rotary joint 906 of FIG. 9 are used in the system shown in FIG. 15. Other configurations, such as those in FIGS. 10, 11, 12 and 14, are similar and are within the scope of this disclosure. As shown in FIG. 15, the sample arm of the swept source OCT/pressure engine 1500 includes a single-mode fiber 912, which feeds into the MCF coupler 904. However, it is possible to split a part of the swept source light from the OCT engine 1500 and feed it into a single-mode/multi-mode mode converter 1502, which converts the single-mode light to multi-mode light. The power split can be achieved by time-division or by a coupler in the OCT optical path. The multi-mode light then passes through a multi-mode circulator 1504 or a multi-mode coupler (not shown) to the MCF coupler 904. The MCF fiber 916 carries the single-mode light through its single-mode core and the multi-mode light through its multi-mode core. Both modes of light pass through an optical rotary joint 906 to the combined OCT/pressure probe 100, passing through the MCF connectors 908 and 910. The single-mode OCT light returning from the probe 100 passes through the rotary joint 906 and the MCF coupler 904, to the single-mode fiber 912, and it is then collected by the OCT engine 1000. The multi-mode light for pressure measurement returning from the probe 100 passes through the rotary joint 906, the MCF coupler 904, the multi-mode circulator 1504, and it is then collected by a photo receiver 1506. The return pressure signal is then digitized by an analog-to-digital converter (A/D) data acquisition system in the OCT engine 1500. In this approach, with minimal modification, the OCT engine 1500 can act as both an OCT engine and a pressure engine, resulting in significant cost savings, because an independent pressure measurement engine is not needed.

Figure 16:
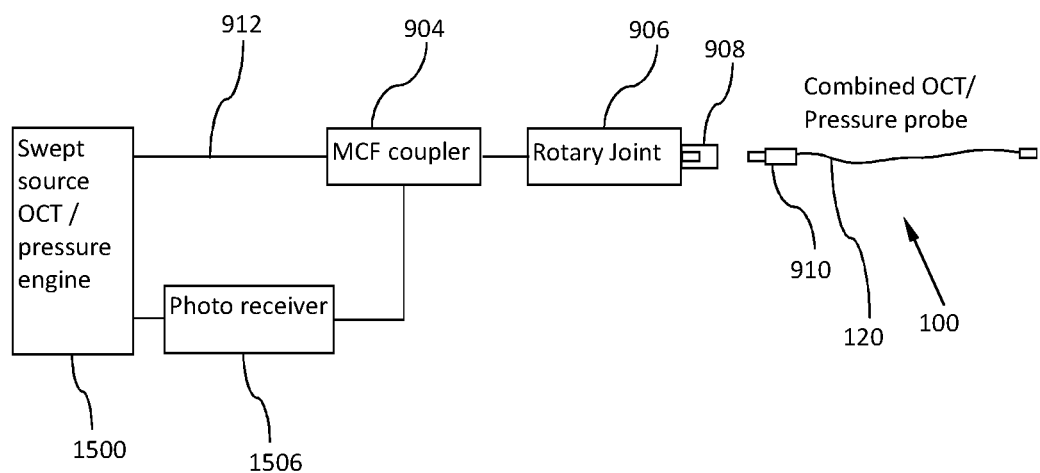

FIG. 16 shows another exemplary combination OCT/pressure measurement system that incorporates an FD-OCT system that uses a swept source. Without loss of generality, the MCF coupler 904 and rotary joint 906 shown in FIG. 9 may be used. The sample arm of the OCT engine 1500 includes a single-mode fiber 912, which feeds into the MCF coupler 904. The OCT excitation light and returned collection light both pass through the single-mode path in the MCF coupler 904 and the rotary joint 906, the connectors 908 and 910 and the combined OCT/pressure probe 100. However, when the single-mode excitation light exits the single-mode core 212 (FIG. 2) in the MCF 120 in the combined OCT/pressure probe 100 and passes through the lens 204, part of the light passes through the optical beam splitter 206 to the optical pressure transducer 210. Light returning 232 from the pressure transducer 210 is collected by the multi-mode core 214 in the MCF 120, and the returning light is redirected by the MCF coupler 904 to a photo receiver 1506. Output of the photo receiver 1506 is digitized by the A/D data acquisition system in the OCT/pressure engine 1500. Compared to FIG. 15, this approach achieves even more cost savings, because the single-mode/multi-mode mode converter 1502 and the multi-mode circulator 1504 of FIG. 15 are omitted.

Figure 17:
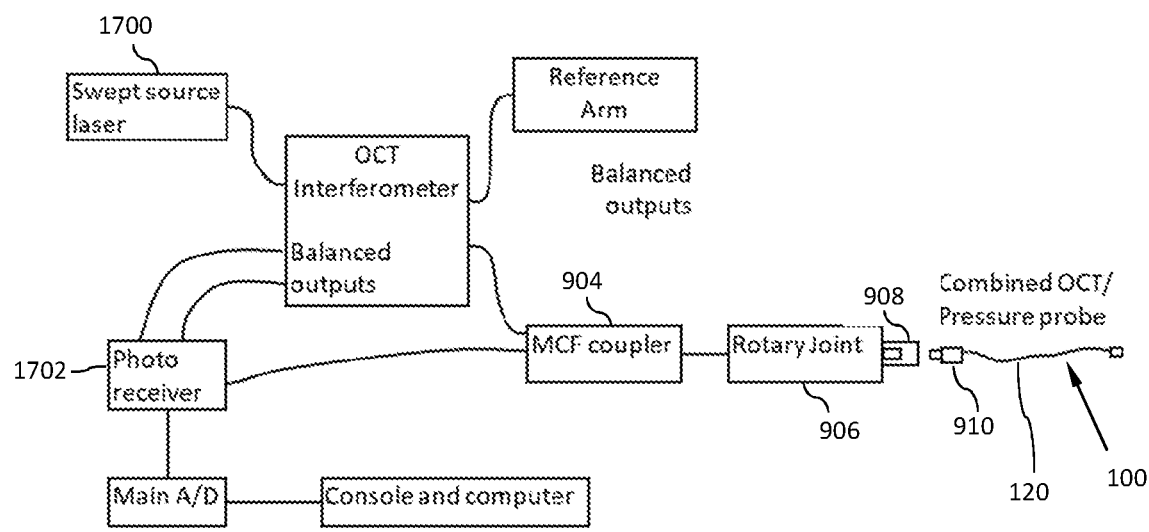

FIG. 17 shows yet another exemplary combination OCT/pressure measurement system that incorporates an FD-OCT system that uses a swept source 1700. To illustrate this arrangement, without loss of generality, the MCF coupler 904 and the rotary joint 906 of FIG. 16 may be used. The apparatus in FIGS. 10 and 11 and other arrangements are similar and are within the scope of this disclosure. The OCT light path is similar to that in the FIG. 16. However, instead of using an independent photo receiver 1506, the collected multi-mode light for pressure measurement shares a photo receiver 1702 with the OCT apparatus. This arrangement results in further cost savings, because it does not need an independent photo receiver.

Figure 18:
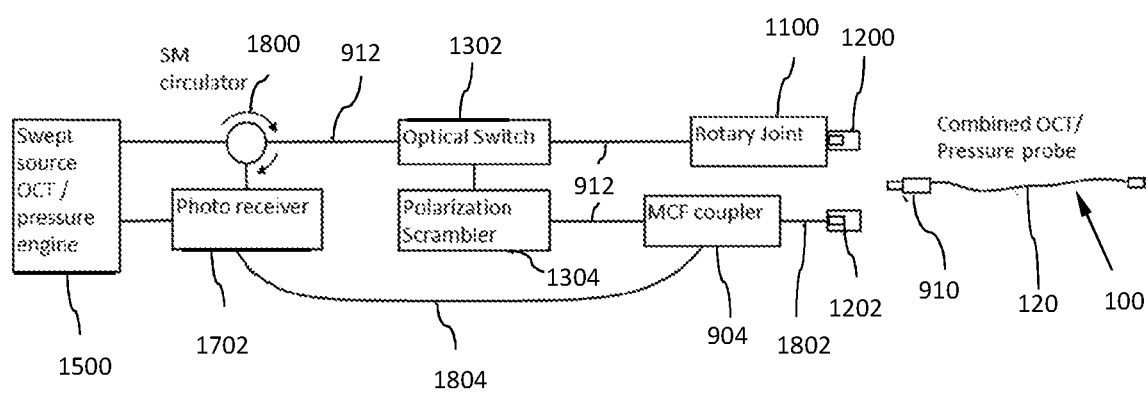

FIG. 18 shows yet another exemplary combination OCT/pressure measurement system that incorporates an FD-OCT system that uses a swept source. In this case, the swept source also provides excitation light for the pressure measurement. The light is transmitted from the swept source in the swept source OCT/pressure engine 1500 to a single-mode circulator (SM circulator) 1800, and to an optical switch 1302. During OCT image acquisition, the optical switch 1302 directs the light to the rotary joint 1100 and on to the combined OCT/pressure probe 100. An OCT signal returning from the combined OCT/pressure probe 100, via the rotary joint 1100, passes through the optical switch 1302 and the single-mode circulator 1800, and is then collected by the photo receiver 1702. During pressure measurement, the optical switch 1302 directs the light to the polarization scrambler 1304. The returned pressure signal passes from the MCF arm 1802 of the MCF coupler 904 to the multi-mode arm 1804, and then the light is collected by the same photo receiver 1702. Lines 912 represent single-mode fibers.

FIGS. 15-18 show exemplary combination OCT/pressure measurement systems that employ FD-OCT systems that use swept sources. These arrangements can be extended to systems that employ other FD-OCT systems, as long as optical frequency information is available, such as in a spectral domain OCT system that uses a broadband light source and a spectrometer.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, module or combination thereof, such as the OCT engine 900, the pressure engine 902, the combined OCT/pressure engine 1300 and/or the swept-source OCT/pressure engine 1500, may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The OCT engine 900, the pressure engine 902, the combined OCT/pressure engine 1300 and/or the swept-source OCT/pressure engine 1500, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective optical fiber cores or claddings from one another and are not intended to indicate any particular order or total number of cores or claddings in any particular embodiment. Thus, for example, a given embodiment may include only a second cladding and a third cladding.

What is claimed is:

1. A combined medical sensor system comprising:
   an optical cable comprising: (a) a single-mode light-carrying region extending from a proximal end of the optical cable to a distal end of the optical cable and (b) a multi-mode light-carrying region extending from the proximal end of the optical cable to the distal end of the optical cable, wherein the multi-mode light-carrying region is not an outer-most cladding;
   an optical coherent tomography (OCT) optical imaging sensor attached proximate the distal end of the optical cable and configured to: (a) be inserted into a lumen of a living being, (b) receive first light exiting a distal end of the single-mode light-carrying region, (c) use the first light to illuminate an interior portion of the lumen, (d) acquire image information about the interior portion of the lumen and (e) transmit an optical signal carrying the image information into the distal end of the single-mode light-carrying region, toward a proximal end of the single-mode light-carrying region; and
   an optical pressure sensor attached proximate the OCT optical imaging sensor and configured to: (a) receive second light from the distal end of the optical cable, (b) sense ambient pressure within the lumen and (c) transmit an optical signal indicative of the ambient pressure into a distal end of the multi-mode light-carrying region, toward a proximal end of the multi-mode light-carrying region.

2. A combined medical sensor system according to claim 1, wherein:
   the single-mode light-carrying region has a first index of refraction;
   the multi-mode light-carrying region has a second index of refraction;
   the optical cable comprises a cladding diametrically outside the multi-mode light-carrying region and having a third index of refraction;
   the second index of refraction is less than the first index of refraction; and
   the third index of refraction is less than the second index of refraction.

3. A combined medical sensor system according to claim 1, wherein:
   the single-mode light-carrying region has a first index of refraction;
   the multi-mode light-carrying region has a second index of refraction;
   the optical cable comprises a first cladding diametrically outside the multi-mode light-carrying region and having a third index of refraction;
   the optical cable comprises a second cladding between the single-mode light-carrying region and the multi-mode light-carrying region and having a fourth index of refraction;
   the third index of refraction is less than the second index of refraction; and
   the fourth index of refraction is less than the first index of refraction and less than the second index of refraction.

4. A combined medical sensor system according to claim 1, wherein the optical cable is configured to optically isolate the single-mode light-carrying region from light in the multi-mode light-carrying region by at least 20 dB at wavelengths between about 400 nm and about 1,700 nm.

5. A combined medical sensor system according to claim 1, wherein the optical cable is configured to optically isolate the single-mode light-carrying region from light in the multi-mode light-carrying region by at least 40 dB at wavelengths between about 400 nm and about 1,700 nm.

6. A combined medical sensor system according to claim 1, wherein the pressure sensor is configured to receive the second light from the distal end of the single-mode light-carrying region.

7. A combined medical sensor system according to claim 6, further comprising an optical splitter optically coupled to the distal end of the single-mode light-carrying region and configured to split light exiting the distal end of the single-mode light-carrying region between: (a) the OCT optical imaging sensor and (b) the pressure sensor.

8. A combined medical sensor system according to claim 7, further comprising a sheath, wherein the OCT optical imaging sensor, the optical pressure sensor and the distal end of the optical cable are disposed within the sheath, the sheath has an outside diameter and a distance between the optical splitter and a furthest reflecting surface of the pressure sensor is less than one-half the outside diameter of the sheath.

9. A combined medical sensor system according to claim 7, wherein the optical splitter comprises a mirror configured to: (a) reflect a first portion, less than all, of the light exiting the distal end of the single-mode light-carrying region to the OCT optical imaging sensor and (b) transmit a second portion, less than all, of the light exiting the distal end of the single-mode light-carrying region through the mirror to the pressure sensor.

10. A combined medical sensor system according to claim 9, wherein the mirror is equally partially reflective over its entire working surface.

11. A combined medical sensor system according to claim 9, wherein:
   a working surface of the mirror is partitioned into a first region and a second region;
   the first region has a first reflectivity and a first transmissivity, wherein the first reflectivity is greater than the first transmissivity, whereby the first region reflects substantially all of the first portion of the light exiting the distal end of the single-mode light-carrying region to the OCT optical imaging sensor; and
   the second region has a second reflectivity less than the first reflectivity and a second transmissivity greater than the first transmissivity, wherein the second transmissivity is greater than the second reflectivity, whereby the second region transmits substantially all of the second portion of the light exiting the distal end of the single-mode light-carrying region through the mirror to the pressure sensor.

12. A combined medical sensor system according to claim 6, further comprising a single light source optically coupled to the proximate end of the single-mode light-carrying region and configured to thereby provide the first light to the OCT optical imaging sensor and the second light to the pressure sensor.

13. A combined medical sensor system according to claim 6, further comprising:
   a first light source optically coupled to the proximate end of the single-mode light-carrying region and configured to thereby provide the first light to the OCT optical imaging sensor; and
   a second light source, distinct from the first light source, optically coupled to the proximate end of the single-mode light-carrying region and configured to thereby provide the second light to the pressure sensor.

14. A combined medical sensor system according to claim 6, further comprising:
   a light source optically coupled to the proximate end of the single-mode light-carrying region and configured to thereby provide the first light to the OCT optical imaging sensor; and
   an optical mode converter optically coupled between the light source and the proximate end of the single-mode light-carrying region and configured to thereby provide multi-mode light to the pressure sensor.

15. A combined medical sensor system according to claim 14, wherein the optical mode converter comprises a polarization scrambler.

16. A combined medical sensor system according to claim 6, further comprising:
   a light source optically coupled to the proximate end of the single-mode light-carrying region and configured to thereby provide the first light to the OCT optical imaging sensor and the second light to the pressure sensor, wherein the first light comprises a first range of wavelengths and the second light comprises a second range of wavelengths that does not overlap with the first range of wavelengths; and
   an optical filter optically coupled between: (a) the distal end of the single-mode light-carrying region and (b) the pressure sensor and configured to: (i) transmit the second range of wavelengths of light to the pressure sensor with a transmissivity of at least about 90% and (ii) transmit the first range of wavelengths of light to the pressure sensor with a transmissivity of at most about 10%.

17. A combined medical sensor system according to claim 16, wherein the light source comprises:
   a first light source configured to provide the first light; and
   a second light source, distinct from the first light source, configured to provide the second light.

18. A combined medical sensor system according to claim 1, wherein the pressure sensor is configured to receive the second light from the distal end of the multi-mode light-carrying region.

19. A combined medical sensor system according to claim 1, further comprising:
   an optical coherence tomography engine optically coupled to the proximal end of the single-mode light-carrying region and configured to receive the optical signal carrying the image information and generate an image therefrom; and
   a pressure measurement engine optically coupled to the proximal end of the multi-mode light-carrying region and configured to receive the optical signal indicative of the ambient pressure and estimate the ambient pressure therefrom.

20. A combined medical sensor system according to claim 19, further comprising:
   a first optical connector configured to be disconnectably optically coupled to the proximal end of the optical cable;
   a second optical connector configured to be disconnectably optically coupled to the proximal end of the optical cable; and
   a switch having at least a first position and a second position; wherein:
   the proximal end of the optical cable is configured to be selectively disconnectably optically coupled to at most one at a time of the first optical connector and the second optical connector;
   the optical coherence tomography engine and the pressure measurement engine have a common optical input port; and
   the switch is optically coupled between the first optical connector, the second optical connector and the common optical input port such that, in the first position, the switch optically couples the first optical connector to the common optical input port and, in the second position, the switch optically couples the second optical connector to the common optical input port.

21. A combined medical sensor system according to claim 1, wherein the multi-mode light-carrying region comprises a plurality of multi-mode light carrying sub-regions, the single-mode light-carrying region being isolated from light in each multi-mode light-carrying sub-region by at least 10 dB at wavelengths between about 400 nm and about 1,700 nm.

22. A combined medical sensor system according to claim 21, wherein the plurality of multi-mode light carrying sub-regions is concentric with the single-mode light-carrying region.

23. A combined medical sensor system according to claim 1, wherein the multi-mode light-carrying region has a numerical aperture greater than about 0.05.

24. A combined medical sensor system according to claim 1, wherein the multi-mode light-carrying region has a numerical aperture between about 0.05 and about 0.5, and the single-mode light-carrying region has a numerical aperture between about 0.05 and about 0.2.

\* \* \* \* \*